(12) United States Patent
Periard Larrivee et al.

(10) Patent No.: US 11,703,438 B2
(45) Date of Patent: Jul. 18, 2023

(54) POROUS MEDIUM PARAMETER MEASUREMENT DEVICE

(71) Applicant: HORTAU INC., Levis (CA)

(72) Inventors: Yann Periard Larrivee, Saint-Luc-de-Bellechasse (CA); Marcellin Duval, Quebec (CA); Vincent Pelletier, Sainte-Henedine (CA)

(73) Assignee: HORTAU INC., Levis (CA)

( * ) Notice: Subject to any disclaimer, the term of this patent is extended or adjusted under 35 U.S.C. 154(b) by 222 days.

(21) Appl. No.: 17/281,185

(22) PCT Filed: Sep. 30, 2019

(86) PCT No.: PCT/CA2019/051395
§ 371 (c)(1),
(2) Date: Mar. 29, 2021

(87) PCT Pub. No.: WO2020/077440
PCT Pub. Date: Apr. 23, 2020

(65) Prior Publication Data
US 2021/0396643 A1    Dec. 23, 2021

Related U.S. Application Data

(60) Provisional application No. 62/747,917, filed on Oct. 19, 2018.

(51) Int. Cl.
*G01N 15/00* (2006.01)
*G01N 15/08* (2006.01)
(Continued)

(52) U.S. Cl.
CPC ..... *G01N 15/0826* (2013.01); *G01N 15/0806* (2013.01); *G01N 33/246* (2013.01)

(58) Field of Classification Search
CPC ......... G01N 15/00–08; G01N 15/0806; G01N 15/0826; G01N 25/56; G01N 33/24; G01N 33/246
See application file for complete search history.

(56) References Cited

U.S. PATENT DOCUMENTS

| 4,068,525 A | 1/1978 | Skaling |
| 6,308,563 B1 | 10/2001 | Hubbell et al. |

(Continued)

FOREIGN PATENT DOCUMENTS

| CA | 2556126 C * | 1/2013 | ........... A01G 25/167 |
| DE | 102009014946 A1 * | 5/2015 | ............. G01N 13/02 |

(Continued)

OTHER PUBLICATIONS

International Search Report of PCT/CA/2019/051395, Search completed on Dec. 2, 2019, Hassan Bayaa.

(Continued)

*Primary Examiner* — Nguyen Q. Ha
(74) *Attorney, Agent, or Firm* — BCF LLP

(57) ABSTRACT

The present technology generally relates to a porous medium parameter measurement device. The porous medium parameter measurement device comprises: a liquid permeable portion comprising a fluid permeable component and a polymer swellable solution; and comprises a gas permeable portion comprising a gas permeable component. The liquid permeable portion is in operative communication with the gas permeable portion through the gas permeable component; and the gas permeable component acts to purge gases from the liquid permeable component and the polymer swellable solution.

20 Claims, 7 Drawing Sheets

(51) Int. Cl.
    *G01N 25/56*    (2006.01)
    *G01N 33/24*    (2006.01)

(56) References Cited

U.S. PATENT DOCUMENTS

| | | |
|---|---|---|
| 6,539,780 B2 | 4/2003 | Hubbell et al. |
| 6,782,909 B1 | 8/2004 | Ragless |
| 2002/0112531 A1 | 8/2002 | Hubbell |

FOREIGN PATENT DOCUMENTS

| | | | |
|---|---|---|---|
| EP | 3655755 A1 | 5/2020 | |
| JP | 2014041054 A | 3/2014 | |
| SU | 966571 A1 | 10/1982 | |
| WO | WO-2006131008 A1 * | 12/2006 | ........... A01G 25/167 |

OTHER PUBLICATIONS

Supplementary European Search Report for corresponding european application No. 19873472, dated Jul. 12, 2022.

\* cited by examiner

POROUS MEDIUM PARAMETER MEASUREMENT DEVICE

CROSS-REFERENCE TO RELATED APPLICATION

This application is a national phase filing under 35 U.S.C. 371 of International Application No. PCT/CA2019/051395, filed on Sep. 30, 2019, which claims the benefit of U.S. Provisional Application No. 62/747,917, filed on Oct. 19, 2018, the disclosure of which is incorporated herein by reference in its entirety.

TECHNICAL FIELD

The present technology generally relates to devices for measuring parameters of a porous medium as well as to methods of using such devices. In particular, the present technology relates to devices for measuring water tension in a porous medium as well as methods of using such devices.

BACKGROUND INFORMATION

As global temperatures reach record highs, severe drought limits the water supply to farms, cities, industries, and ecosystems. Strategies must be put in place to optimize the use of water and to avoid water waste. Over-irrigation of soils can contribute to water shortages and suppress biodiversity by leaching nutrients that cause eutrophication. Improving and optimizing irrigation accuracy could thus provide significant environmental and economic benefits worldwide.

Several soil parameters may be affected by the soil's water tension. Soil parameter measurement devices and/or instruments have been used to measure soil water tension (SWT) and to derive optimal irrigation schedules. Unfortunately, current soil parameter measurement devices and/or instruments present several problems. One such problem is caused by the fact that exchange of water between the instrument and the soil works only to a specified negative pressure (suction, matric potential) of the ceramic tip. For example, a ceramic tip with an air entry value of 80 cb experiencing a matric potential of 100 cb will allow air to migrate into the instrument tube. As soon as this occurs, the negative pressure of the instrument will rapidly drop to a value close to 0 cb, and the measurement of the instrument will not reflect the real prevailing matric potential of 100 cb and hence the instrument is not useable in such conditions. To rectify this situation, the instrument tube has to be re-filled with water. A hand vacuum pump attached to the top of the instrument tube has to be operated to draw soil water through the ceramic tip of the instrument to purge any trapped air bubbles within the ceramic tip with water. Because of problems like this, current instruments require frequent maintenance to ensure accuracy of the measurements.

Another problem frequently observed with instruments such as tensiometers which affects the measurements is caused by air bubbles appearing inside the water-filled tube connecting the porous tip to the pressure measurement device. This occurs because of the reduced solubility of gases at lower hydrostatic pressure (as well as higher temperatures) and also because of the diffusion of gases from the air phase of the unsaturated soil trough the porous walls of the tensiometer tip.

Being able to precisely and accurately measure parameters of a porous medium such as, for example, soil, is of critical importance to derive irrigation schedule of cultures. It is thus an object of the present technology to provide porous medium parameter measurement device that alleviate at least some of these problems and that allow to provide more accurate measurements of the parameters.

SUMMARY OF THE DISCLOSURE

In various aspects, the present technology relates to a porous medium parameter measurement device comprising: i) a liquid permeable portion comprising a fluid permeable component and a polymer swellable solution; ii) a gas permeable portion comprising a gas permeable component; wherein the liquid permeable portion is in operative communication with the gas permeable portion through the gas permeable component; and wherein the gas permeable component acts to purge gases from the liquid permeable component and the polymer swellable solution.

Other aspects and features of the present disclosure will become apparent to those ordinarily skilled in the art upon review of the following description of specific embodiments.

BRIEF DESCRIPTION OF THE DRAWINGS

Further aspects and advantages of the present technology will become better understood with reference to the description in association with the following in which:

FIG. 3A: inner chamber 164 comprises polymer swellable solution;

FIG. 3B: inner chamber 164 comprises porous medium solution;

DETAILED DESCRIPTION

Figure 1:
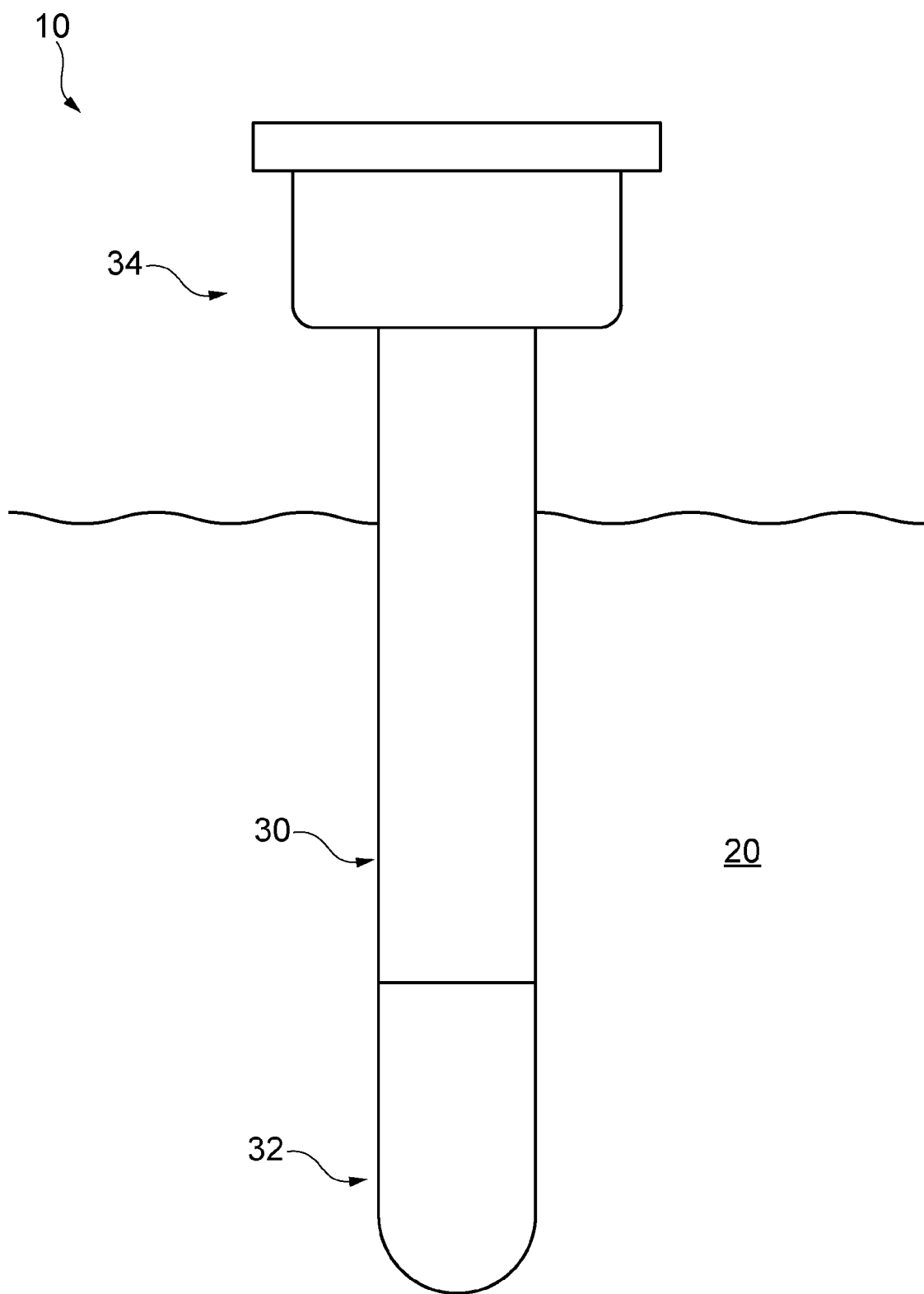
FIG. 1 is a schematic side perspective view of a porous medium parameter measurement device according to one embodiment of the present technology.

Before continuing to describe the present disclosure in further detail, it is to be understood that this disclosure is not limited to specific devices, systems, methods, or uses or process steps, and as such they may vary. It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is to be understood that positional descriptions such as "above", "lower", "upper", "below", "forward", "rearward" "left", "right" and the like should, unless otherwise indicated, be taken in the context of the figures and correspond to the position and orientation of the porous medium parameter measurement devices and corresponding parts when inserted in the porous medium, with the "upper" corresponding to a portion closer to the exposed surface of the porous medium and the "lower" corresponding to a portion opposed to the upper portion.

As used herein, the expression "porous medium" refers to a material containing pores, cavities, channels, voids or a combination thereof. The skeletal portion of the material is referred to herein as the "material body" or "matrix". The pores, cavities, channels or voids are filled with fluids (i.e., liquid, gas) and/or solid components of the porous medium. The porous medium may be characterized by one or more of its porosity, permeability, tensile strength, electrical conductivity, pH, temperature, and tortuosity. The porous medium may be of different nature and comprise different components in various proportions. Many natural substances such as rocks and soil (e.g., aquifers, petroleum reservoirs), zeolites, biological tissues (e.g. bones, straw, wood, cork), and man made materials such as cements and ceramics can be considered as porous media. Further examples of porous media include, but are not limited to, earthen soil or greenhouse soil. The porous medium may be a soil for crop production, which can comprise for instance, sand, peat, bark, coconut fibers, loam, silt, clay, and the like, each in various proportions. The porous medium may also be a porous medium comprising organic and inorganic compounds in various proportions, and be used for instance as a growing medium for greenhouses, nursery production, landscaping and urban agriculture. Soils other than those for crop production are also within the scope of the expression "porous medium".

The porous medium can also include a variable content of a water-based solution, for example, a solution eventually leaching out of the porous medium to form the porous medium solution which comprises fluids and/or dissolved ionic species and/or other components of the porous medium.

As used herein, the terms "connected", "coupled", "operatively connected" or "in communication" refers to any connection or coupling, either direct or indirect, between two or more elements. The connection or coupling between the elements may be mechanical, physical, biological, optical, operational, and electrical or a combination thereof.

The term "hydrogel" as used herein refers to a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content.

The expression "soil water tension" or "SWT" herein refers to the force necessary for plant roots to extract water from the soil.

As used herein, the term "fluid" includes both liquids and gases. As used herein, the term "gas" refers to a fluid (such as, but not limited to, air) that has neither independent shape nor volume but tends to expand indefinitely, whereas the term "liquid", as used herein, refers to a fluid (such as, but not limited to, water) that is nearly incompressible and that conforms to the shape of its container but retains a (nearly) constant volume independent of pressure.

As used herein, the term "tensiometer" refers to a measuring instrument for determining the matric water potential (i.e., soil moisture tension) in the vadose zone.

As used herein, the term "cavitation" refers to hydrodynamic cavitation which is the process of vaporization, bubble generation and bubble implosion which occurs in a flowing liquid as a result of a decrease and subsequent increase in local pressure. Cavitation occurs when the local pressure declines to some point below the saturated vapor pressure of the liquid and subsequent recovery above the vapor pressure. If the recovery pressure is not above the vapor pressure then flashing is said to have occurred. Hydrodynamic cavitation can be produced by passing a liquid through a constricted channel at a specific flow velocity or by mechanical rotation of an object through a liquid. The process of bubble generation, and the subsequent growth and collapse of the cavitation bubbles, results in high energy densities and in high local temperatures and local pressures at the surface of the bubbles for a very short time.

Several soil parameters are important in order to maintain optimal crop production. Soil parameters are influenced by concentration of different ionic species in the soil solution which is present in the pores and interstices of the porous soil matrix. This soil water needs to be accessed in order to measure parameters of the soil solution. Up to now, suction lysimeter/sphygmomanometer has been used to achieve this. However, such devices/techniques present some drawbacks at least in that saturated soil solution must be maintained. This difficulty is caused by the fact that when a solution is subjected to negative pressure, it will frequently undergo a change of phase even at room temperature (approximately 25° C.). This phenomenon of heterogeneous cavitation is amplified when the water is not pure and comprises gases. This problem is amplified even more when gases accumulate by diffusion in the porous components and/or in the water reservoir of a tensiometer (e.g., ceramic portion). In standard tensiometers, data becomes inaccurate when soil tension reaches a value of between about 60-80 kPa. When such tension is reached, cavitation occurs in the water reservoir and in the ceramic. In the long term, even if a pressure of 60 kPa is not reached, gases will diffuse and eventually partially desaturate the ceramic thereby causing significant delays in response time. If the ceramic reaches an air entry point of 1000 kPa, it will become desaturated. When this critical point is reached, pressure inside becomes equal to the atmospheric pressure. From this point on, the pressure sensor of the tensiometer has to compensate for the atmospheric pressure and displays 0 kPa. To reinitiate the tensiometer, it is necessary to create a vacuum to remove gases present in the ceramic and to fill the water reservoir.

The present technology stems from the discoverers' elucidation that the use of a gas permeable component which exhibit high permeability to gases and low permeability to water in simultaneously contact with: i) the exterior environment of the porous medium parameter measurement device (i.e., in contact with the porous medium) and ii) a liquid permeable component and/or a polymer swellable solution of the device, allows rapid evacuation of gases from the device. In absence of this rapid evacuation, as seen in current devices, gases remain trapped in the fluid permeable component for longer periods, thereby creating overpressure. The discoverers have uncovered that with this feature rapid stabilization of the system is achieved which is not observed with current devices.

In view of the above, one aspect of the present technology is to provide a porous medium parameter measurement device (PMPM) device that allows to measure water tension as well as other parameters that are related to or affected by water tension (i.e., water tension related parameters), such as, but not limited to: ionic concentration, in the porous medium.

Although some of the embodiments of the present technology will be explained and described herein in relation to PMPM device that measures water tension in soil (e.g., tensiometer), it will be appreciated that the various features, functionalities and advantages of the present PMPM device may be applied to measure other parameters or characteristics of a porous medium (e.g., ionic concentration of $NO_3^-$, $PO_4^{3-}$, $K^+$, $NH_4^+$, $Ca^{2+}$, $Mg^{2+}$, $Na^+$, or Cl) as will be better explained further herein.

FIG. 1 shows the overall general structure of a porous medium parameter measurement device according of the present technology. In this embodiment, the porous medium parameter measurement (PMPM) device is generally depicted as 10 and is placed into a porous medium 20 (e.g., soil). The PMPM device 10 comprises a housing 30 having an elongated shape to facilitate insertion of the PMPM device 10 into the porous medium 20. The housing 30 may preferably have a hollow interior so as to accommodate certain components of the device. The housing 30 comprises a lower end 32 which, in used, is inserted in the porous medium 20 and an upper end 34 which, in use, is the component of the device that is the closest to the surface of the porous medium 20. The housing 30 is airtight sealed or airtight sealable at its upper end 34. It will be appreciated that the PMPM device 10 may be configured with various other shapes and forms without departing from the present technology.

Figure 2:
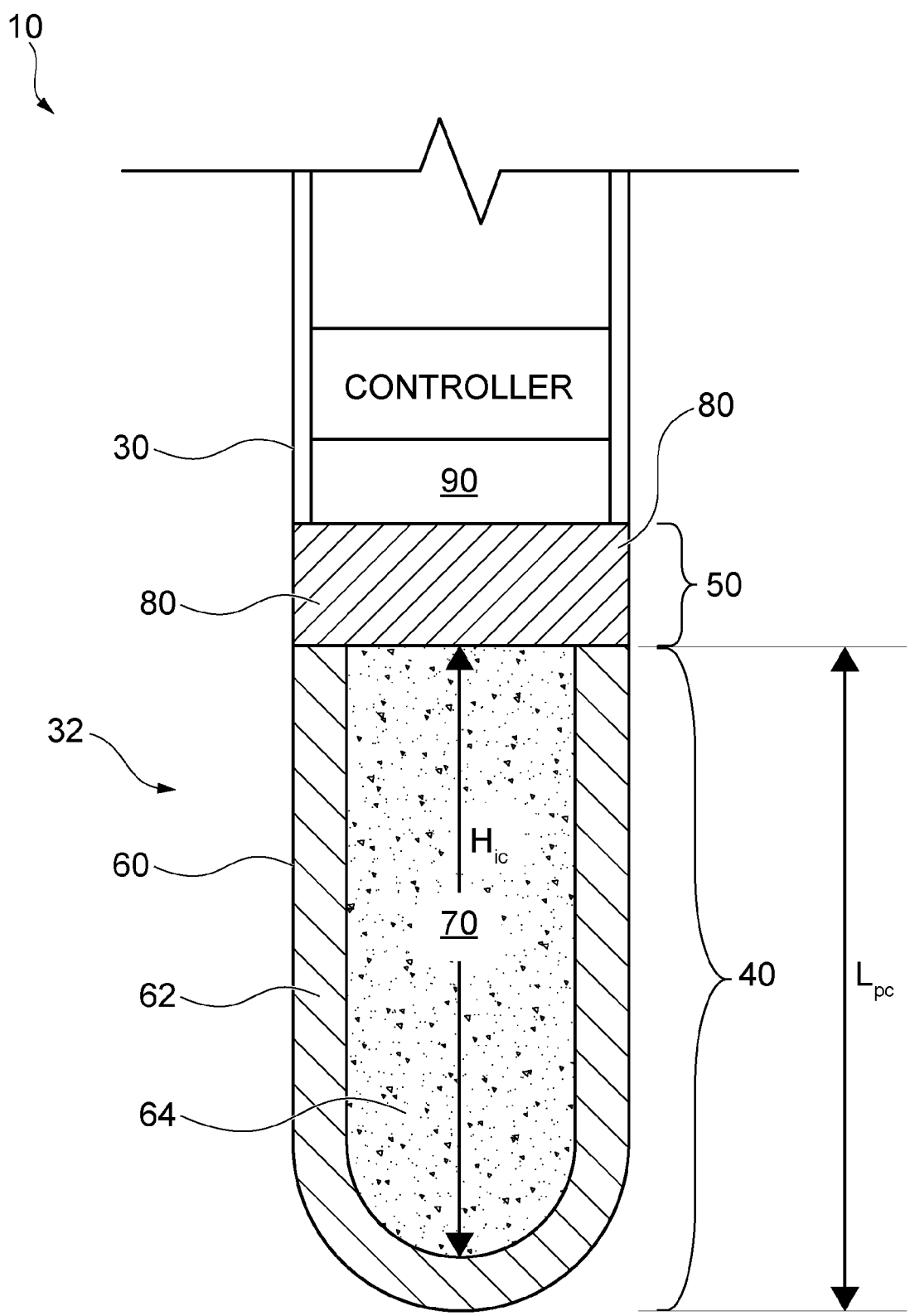
FIG. 2 is a schematic cross-sectional side perspective view of the lower portion of a porous medium parameter measurement device according to another embodiment of the present technology.

FIG. 2 shows an enlarged view of the lower portion 32 of the PMPM device 10. The lower end 32 of the housing 30 comprises a liquid permeable portion 40 which is substantially impermeable to air and a gas permeable portion 50 which is substantially impermeable to liquid (e.g., low permeability to liquid). The liquid permeable portion 40 is in operative communication, for instance in gas communication, with the gas permeable portion 50. In some instances, the liquid permeable portion 40 is in contact with the gas permeable portion 50, wherein at least a part of the liquid permeable portion 40 is in contact with at least a part of the gas permeable portion 50 to ensure operative communication between portions 40, 50.

The liquid permeable portion 40 comprises a liquid permeable component 60 having a liquid permeable wall 62 defining an inner chamber 64. Inner chamber 64 comprises (e.g., is filled with) a polymer swellable solution 70. A pressure sensor 90 is in operational communication with the inner chamber 64 so as to measure pressure inside inner chamber 64. Liquid permeable component 60 is made from a porous material that while being permeable to liquids is substantially impermeable to gas (e.g., air) and substantially impermeable to the polymers of the polymer swellable solution 70. In some instances, the porous material is ceramic, for instance, hydrophilic ceramic. The ceramic used in the fabrication of liquid permeable component 60 may exhibit an air entry point that is below the maximum pressure (induced by the polymer concentration). For example, the air entry point is between about 25 kPa and about 2000 kPa, or is about 1100 kPa.

In some other instances, the porous material is made of plastic or stainless or any other materials.

In some instances the fluid permeable component 60 has a length ($L_{pc}$) measured from the lower most end of the fluid permeable component 40 to the upper most point of the fluid permeable component 40. $L_{pc}$, is between about 50 mm and about 100 mm, or between about 60 mm and about 75 mm or a length of about 65 mm. In some instances, fluid permeable component 60 has an outer diameter of between about 15 mm and about 25 mm; or between about 17 mm and about 22 mm, or an outer diameter of about 19 mm. The walls 62 have an average thickness of between about 2 mm and about 5 mm, or between about 3 mm and about 4 mm, or an average thickness of about 4 mm. In some other instances, the fluid permeable component 60 has a length of about 65 mm, an outer diameter of about 19 mm and a thickness of wall 62 of about 4 mm.

The inner chamber 64 is suitable for accepting the polymer swellable solution 70. In some instances, the inner chamber 64 has a height (HO that is between about 0.2 mm and about 75 mm, or between about 1 mm and about 60 mm, or between about 5 mm and about 60 mm. In some instances, the inner chamber 64 has a volume that is between about 0.5 $cm^3$ and about 7 $cm^3$, or between about 0.5 $cm^3$ and about 6.5 $cm^3$.

In some implementations of these embodiments, the liquid permeable component 60 has a conical shape. It is to be understood that the liquid permeable component 60 may have other shapes without departing from the present technology such as, for example: a toric shape, a cubic shape, a spherical shape, or a disc-like shape.

The polymer swellable solution 70 comprises a polymer, preferably a water soluble polymer, more preferably a non-ionic water-soluble polymer. In some instances, the polymer present in the polymer swellable solution 70 has one or more of the following properties: i) hydrophilic; ii) non-pH sensitive, iii) high absorption rate; iv) low propensity to drying; v) chemical stability, and vi) mechanically robustness.

Examples of polymers that may be present in the polymer swellable solution of the present technology include, but are not limited to: superabsorbents; hydrogels such as for example: poly(2-hydroxyethyl methacrylate), N-vinylpyrrolidone, copolymer of 2,3-dihydroxypropyl methacrylate, 2-hydroxyethyl methacrylate, polyethylene glycol (PEG) polyvinyl pyrrolidinone gold (PVP), poly (vinyl alcohol) (PVA), poly (N-isopropylacrylamide), poly (acrylamide-co-diallyldimethylammonium chloride), sucrose derivative and cellulose. Further examples of polymers include: non-ionic polyacrylamides.

Other examples of polymers that may be present in the polymer swellable solution of the present technology include, but are not limited to: acrylic acid, methacrylic acid, 2-bromoacrylic acid, 2-(bromomethyl) acrylic acid, 2-ethylacrylic acid, methacrylic acid, 2-propylacrylic acid, sodium acrylate, sodium methacrylate or any derivatives thereof, sodium hydroxide, or homopolymers, heteropolymers or any derivatives thereof polymerized with a crosslinker of di-acrylate, di-acrylamide, and di-vinyl, alkylacrylamide, N-(3-aminopropyl)methacrylamide hydrochloride, N-tert-butylacrylamide, diacetone acrylamide, N,N-diethylacrylamide, N,N-diethylmethacrylamide, N,N-dimethylacrylamide, N-[3-(dimethylamino)propyl]methacrylamide, N-ethylacrylamide, N,N'-eexamethylenebis (methacrylamide), N-hydroxyethylacrylamide, N-(hydroxymethyl) acrylamide, (4-hydroxyphenyl)methacrylamide, 2-hydroxypropyl)-methacrylamide, N-(isobutoxy methyl) acrylamide, N-isopropylacrylamide, N-isopropylacrylamide, N-isopropylmethacrylamide, methacrylamide, or homopolymers, heteropolymers or derivatives thereof polymerized with a crosslinker of di-acrylate, di-acrylamide, and di-vinyl.

Other examples of polymers that may be present in the polymer swellable solution of the present technology include, but are not limited to: copolymers of maleic anhydride copolymer, polyvinyl alcohol copolymers, crosslinked polyethylene oxide, crosslinked carboxymethylcellulose or starch grafted copolymer.

In some embodiments, the concentration of polymers in the polymer swellable solution of the present technology is between about 5 wt % and about 90 wt %, or between about 10 wt % and about 70 wt %, or between about 10 wt % and about 30 wt %. In some embodiments, the concentration of polymers in the polymer swellable solution of the present technology is at least about 5 wt %, at least about 10 wt %, at least about 15 wt %, at least about 20 wt %, at least about 25 wt %, at least about 30 wt %, at least about 35 wt %, at least about 40 wt %, at least about 45 wt %, at least about 50 wt %, at least about 55 wt %, at least about 60 wt %, at least about 65 wt %, at least about 70 wt %, at least about 75 wt %, at least about 80 wt %, at least about 85 wt %, or at least about 90 wt %.

In some embodiments, the PMPM device comprises a polymer swellable solution in an amount ranging from between about 2 g polymer/L solution (e.g., water), or between about 500 g polymer/L solution (e.g., water), or between about 2 kg polymer/L solution (e.g., water).

In some embodiments, the liquid permeable portion 40 is in operative communication with the gas permeable portion 50 via the gas permeable component 80. Such operative communication is achieved when the gas permeable component 80 is in contact with the exterior environment of the device 10 (i.e., with the porous medium) and the porous material of the liquid permeable component 60. In some other embodiments, the operative communication is achieved when the gas permeable component 80 is in contact with the exterior of environment of the device 10 (i.e., with the porous medium) and with the polymer swellable solution 70. In some other embodiments, the operative communication is achieved when the gas permeable component 80 is in contact with the exterior of environment of the device 10 (i.e., with the porous medium), the porous material of the liquid permeable component 60 and with the polymer swellable solution 70. For example, the gas permeable component 80 may be part of the wall of the housing 30, or it may be integrated into the wall of the housing 30, or it may be part of the fluid permeable component 60.

In some instances, the gas permeable component 80 comprises a plurality of pores having an average size that ranges between about 5 microns and about 50 microns, or between about 5 microns and 35 microns, or between about 10 microns and about 50 microns, or between about 10 microns and about 35 microns. The gas permeable component 80 purges gas (e.g., air/air bubbles) which is trapped into the polymer swellable solution 70 and/or trapped into the liquid permeable component 60. In some instances, this purging action is achieved shortly after the polymer has started swelling (i.e., upon contact with the porous medium solution entering the inner chamber 64). In some instances, the polymer forms a hydrogel upon contact with the porous medium solution entering the inner chamber. This rapid removal of gas (e.g., air/air bubbles) improves the overall homogeneity of the polymer swellable solution 70. In some instances, the gas permeable component 80 prevents leakage of the polymers out of the polymer swellable solution 70.

In some implementations, the gas permeable component 80 is highly gas permeable and poorly permeable to water (e.g., hydrophobic) which facilitates evacuation of gas from the liquid permeable component 60 and/or from the polymer swellable solution 70. The gas permeable component 80 may be made of a porous hydrophobic material having an average pore size that prevents the polymer molecules from passing through the hydrophobic material. For instances, the hydrophobic material may be a hydrophobic membrane, a hydrophobic sheath, a hydrophobic film, or the like. Preferably, the hydrophobic material is suitable to retain the polymer molecules in the liquid permeable portion 40 of the device 10. In these instances, the average pore size of the hydrophobic material is smaller than the size of the polymer molecules.

In some instances, the hydrophobic material includes, but is not limited to, polyethylene, and polyethylene co-polymers. The polyethylene or the polyethylene co-polymers may have an average pore size of between about 10 and 200 microns. A person skilled in the art will readily appreciate that other materials may be included in the hydrophobic material without departing from the present technology.

Various configurations of the liquid permeable portion 40 and of the gas permeable portion 50 may be envisioned without departing from the present technology. Examples of other configurations are depicted in FIGS. 3 to 6.

Figure 3A:
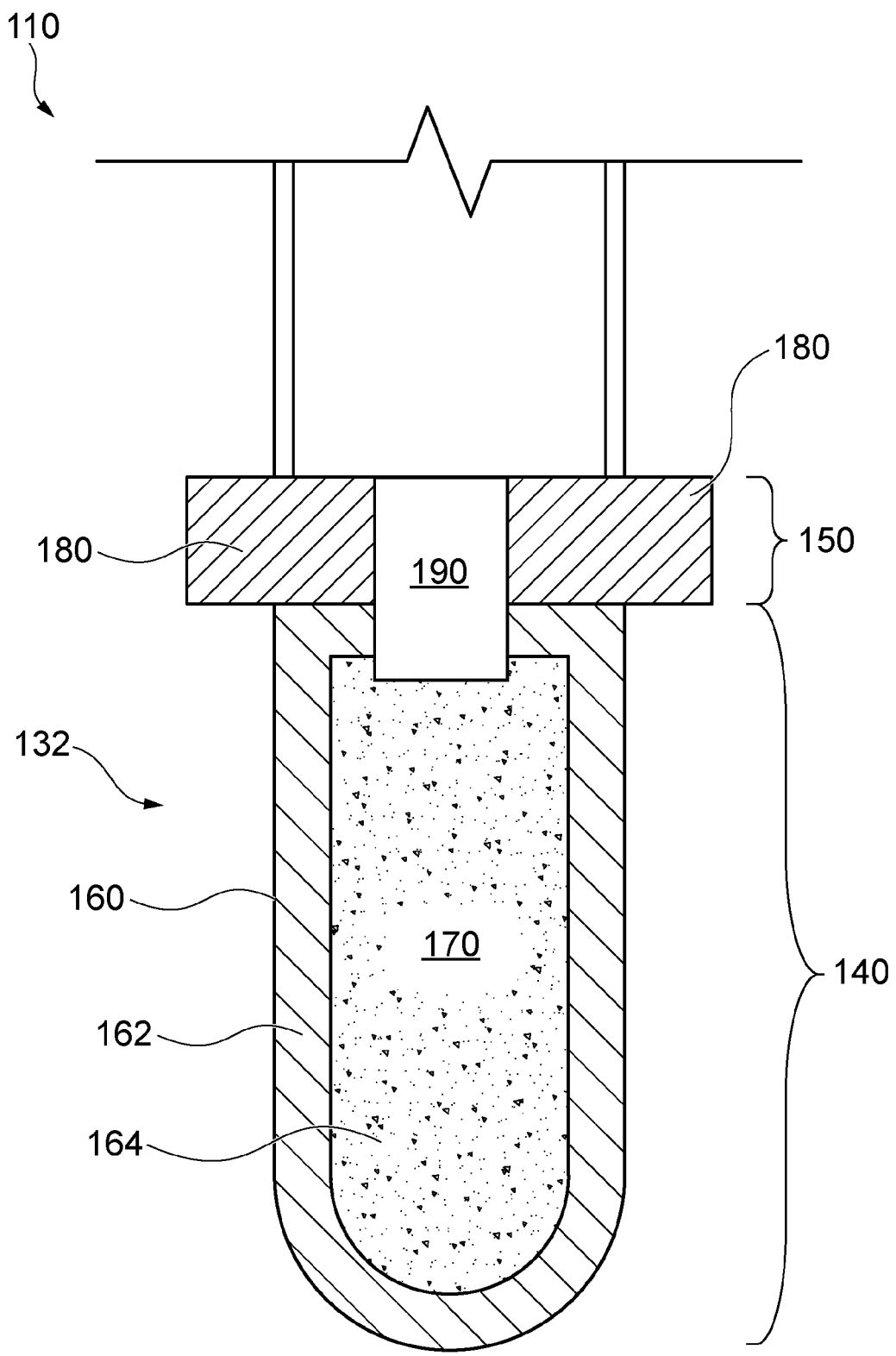
FIGS. 3A-3B are schematic cross-sectional side perspective views of a lower portion of a porous medium parameter measurement device according to another embodiment of the present technology.
Figure 3B:
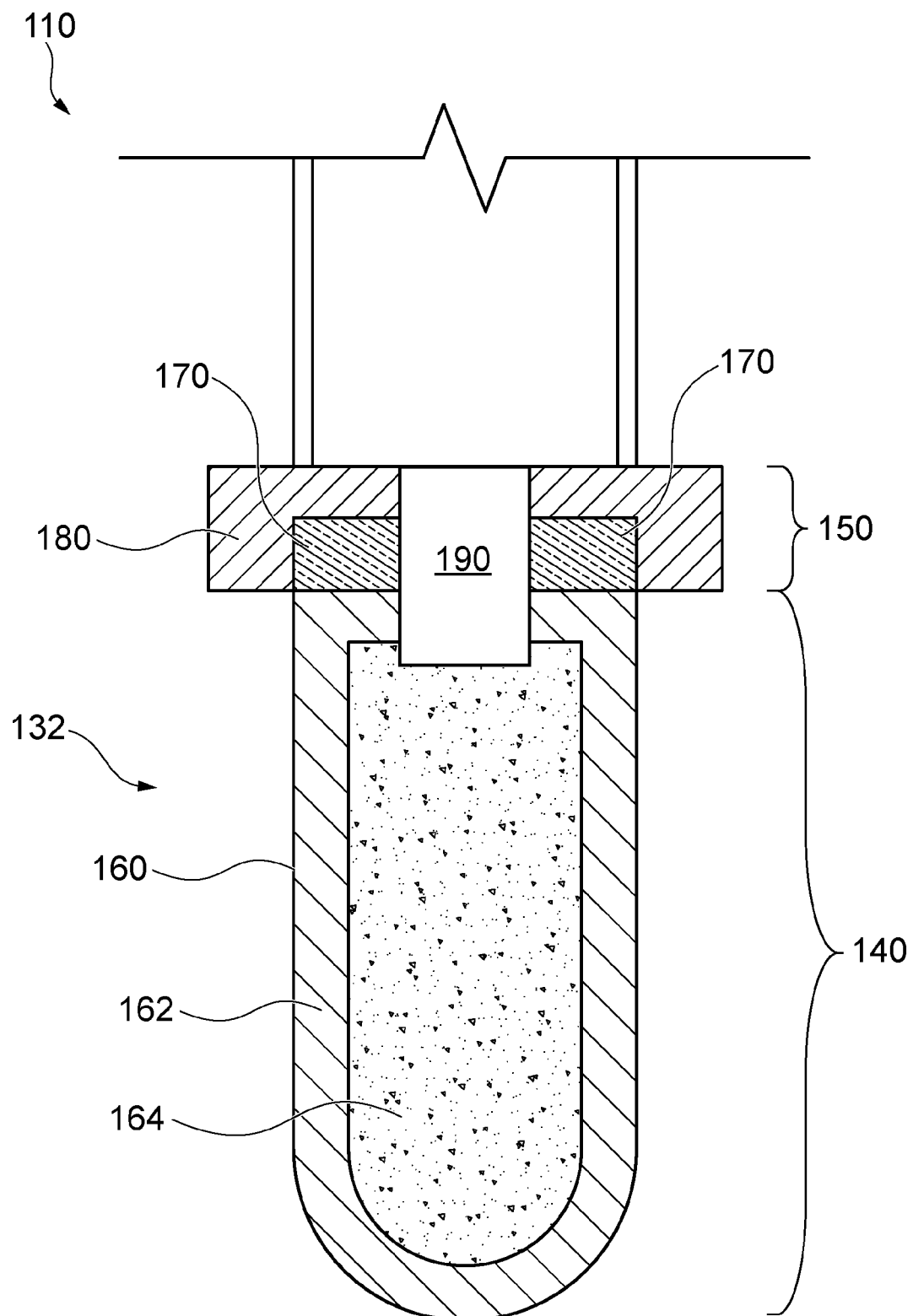

FIG. 3A shows the lower portion 132 of the PMPM device 110 according to another embodiment of the present technology wherein the porous medium parameter measurement device 110 comprises a gas permeable portion 150 located on top the liquid permeable portion 140. In this embodiment, gas permeable component 180 is in contact with the exterior environment of the porous medium parameter measurement device 110 (i.e., porous medium) (in use) as well as in contact with the liquid permeable component 160 having wall 162. In this configuration, the gas permeable component 180 is not in direct contact with the polymer swellable solution 170 which is present in the inner chamber 164 and evacuation of gases from the liquid permeable component 160 occurs without these gases having to pass through the polymer swellable solution 170. In such embodiment, the porous medium parameter measurement device 110 comprises a pressure sensor 190. Pressure sensor 190 is in operational configuration with the inner chamber 164 so as to measure pressure inside inner chamber 164. In another configuration of this embodiment, such as depicted in FIG. 3B, the inner chamber 164 comprises a porous medium solution lacking polymers (e.g., porous medium solution). In some instances, the polymer swellable solution 170 is found elsewhere in the device. For example, as seen in FIG. 3B, the polymer swellable solution 170 may be found between the liquid permeable component 160 and the gas permeable component 180.

Figure 4:
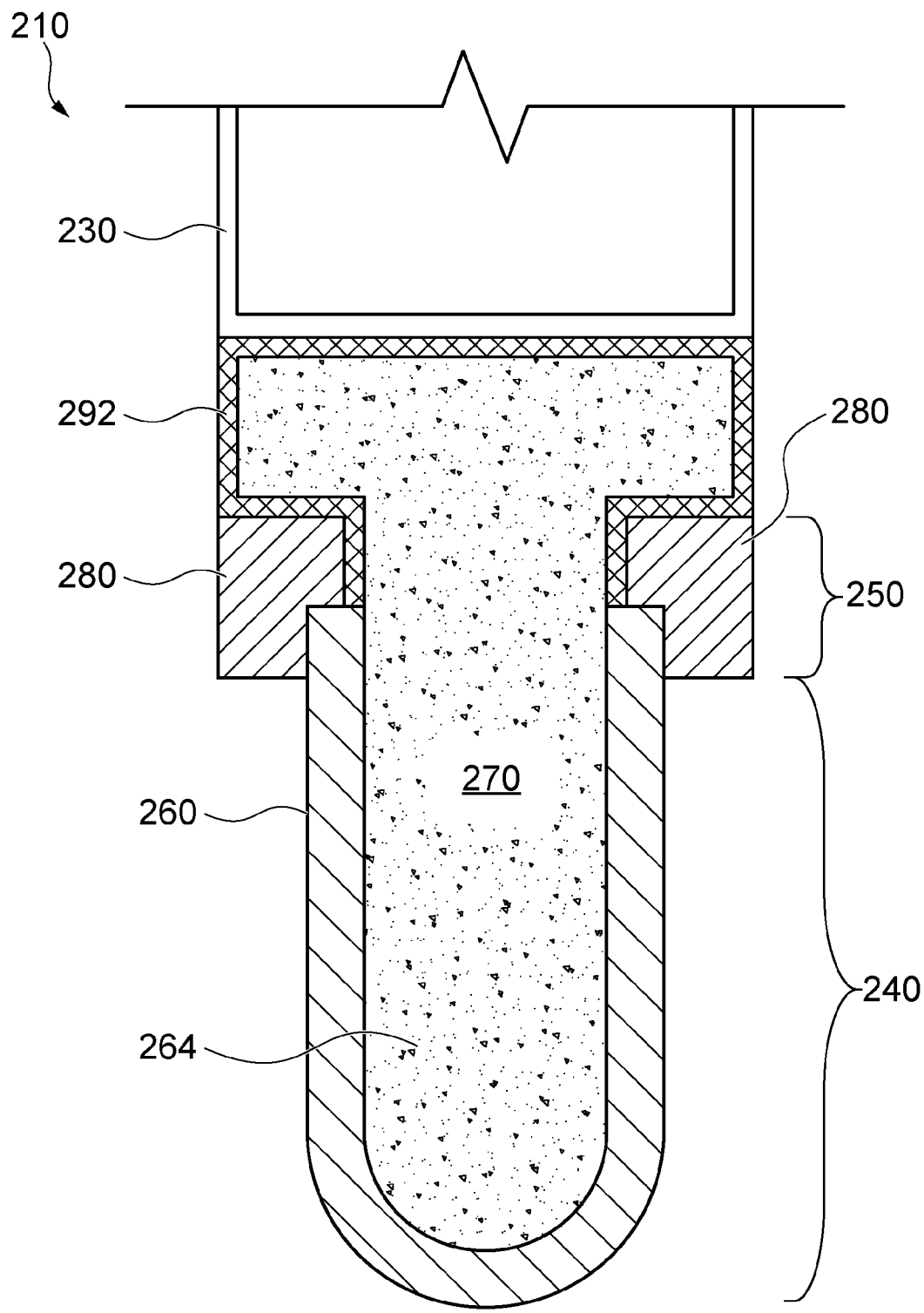
FIG. 4 is a schematic cross-sectional side perspective view of a lower portion of a porous medium parameter measurement device according to yet another embodiment of the present technology.

FIG. 4 shows another embodiment of the PMPM device of the present technology wherein the PMPM device 210 comprises a gas permeable portion 250 located adjacent the liquid permeable portion 240. In this embodiment, the gas permeable component 280 is in contact with the exterior environment of the PMPM device 210 (i.e., porous medium) when in use as well as in contact with the liquid permeable component 260 while not in direct contact with the polymer swellable solution 270 in the inner chamber 264. The polymer swellable solution 270 is separated from the gas permeable component 280 by the fluid impermeable lining 292. In some instances, the fluid impermeable lining 292 is made of materials such as, but not limited to, plastic, aluminum, stainless or the like.

Figure 6:
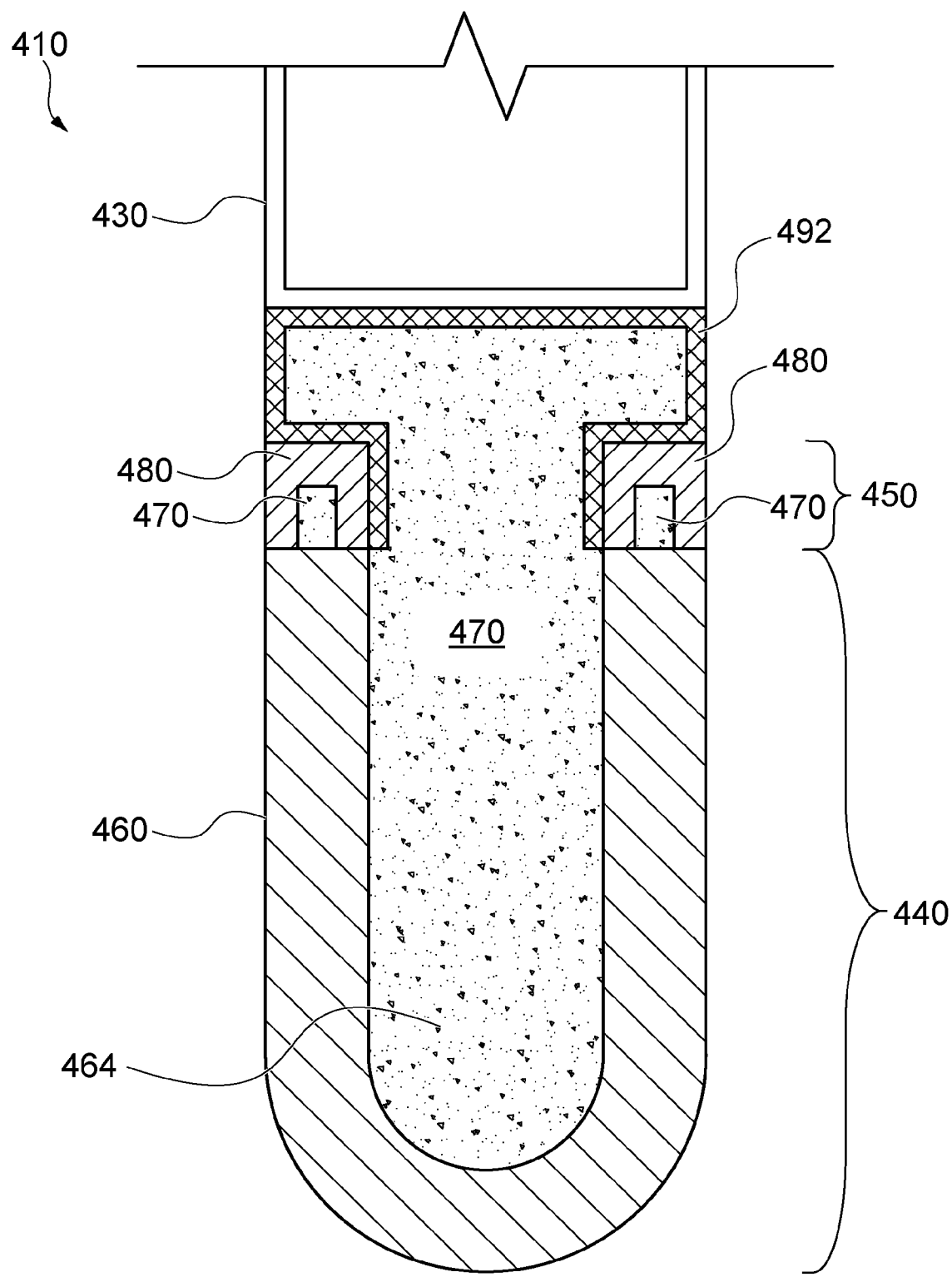
FIG. 6 is a schematic cross-sectional side perspective view of a lower portion of a porous medium parameter measurement device according to another further embodiment of the present technology.

The PMPM device 410 depicted in FIG. 6 has a configuration that is similar to the configuration of the PMPM device 210 of FIG. 4. However, in the configuration depicted in FIG. 6 a portion of the polymer swellable solution 470 is present within the gas permeable component 480. The remaining portion of the polymer swellable solution 470 is separated from the gas permeable component 480 by a fluid impermeable lining 492.

Figure 5:
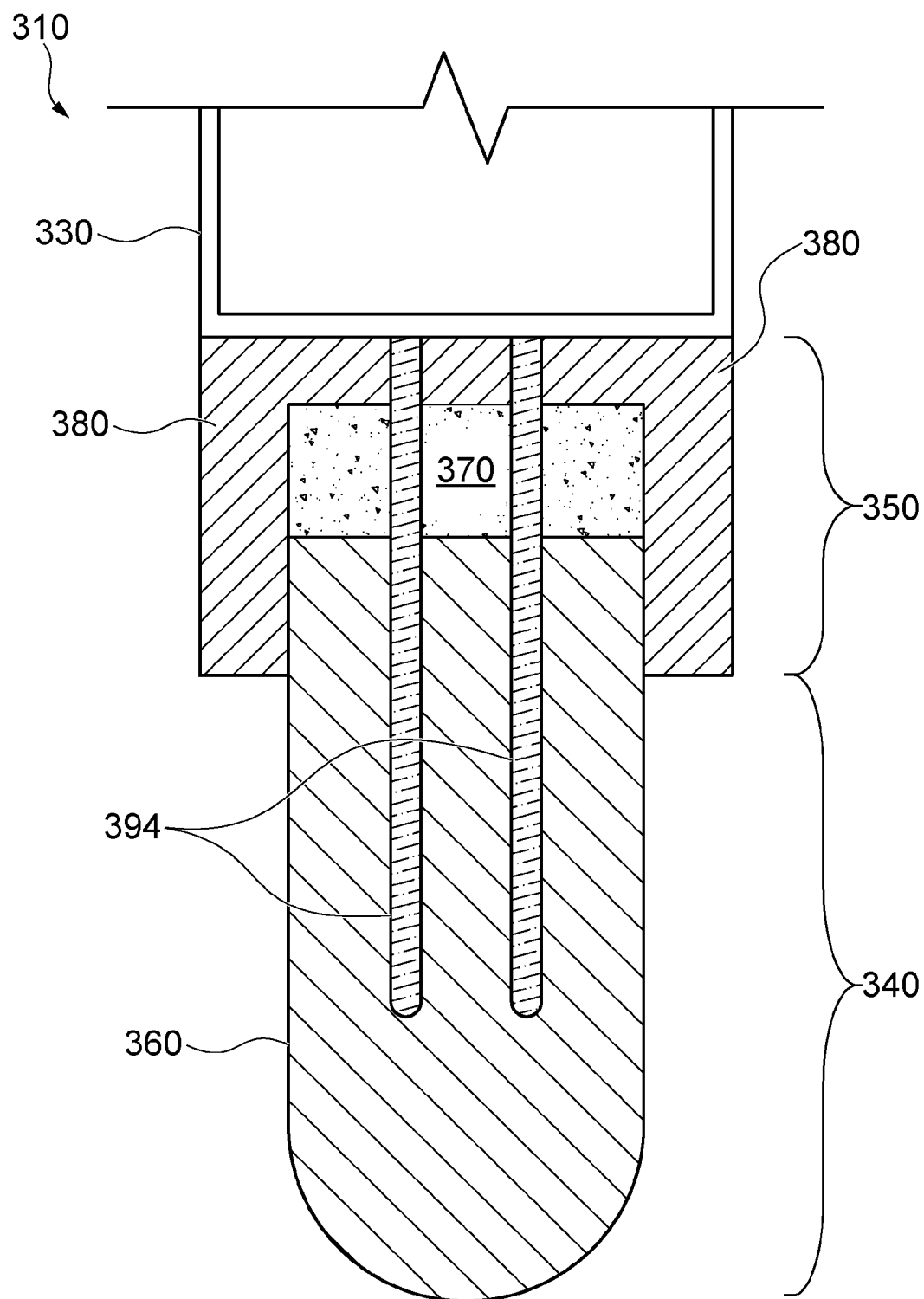
FIG. 5 is a schematic cross-sectional side perspective view of a lower portion of a porous medium parameter measurement device according to a further embodiment of the present technology.

In the PMPM device 310 depicted in FIG. 5, the gas permeable component 380 is in contact with the exterior environment of the PMPM device 310 (i.e., porous medium) when in use, the liquid permeable component 360 and with the polymer swellable solution 370. In this embodiment, the polymer swellable solution 370 is present between the liquid permeable component 360 and the gas permeable component 380. In some implementations of this embodiment, the PMPM device 310 comprises a sensing device 394 such as, for example, capacitive sensing devices (e.g., electrodes) for measuring ions present in the liquid permeable portion 340. Other sensors may be envisioned such as sensors for assessing, salinity, nitrate, pH, presence/concentration of organic substances, nutrients, organic or inorganic contaminants, petroleum products, or the like. Other detection apparatus may be used, such as, but are not limited to, apparatus for optical measurements by absorbance, transmittance, luminescence, spectroscopy, spectroscopy (Raman, SERS), apparatus for electrochemical measurements by standard specific ion electrodes (ISE) or microelectronic adaptations (labchip, chip technologies, etc), field effect transistor (FET), apparatus for sensitive field effect transistor electrochemical measurements, chemical field effect transistor, electrolyte oxide semiconductor field effect transistor, metal oxide semiconductor field effect transistor, enzymatic field effect transistor, apparatus for chemical or electrochemical reactions on electrodes with suitable surfaces (polymer, nanoparticles, etc.) winch may be measured by optics (optodes, optrodes, etc.), apparatus for direct electrical measurements (resistance, conductivity, voltammetry, amperometry, capacitive, potentiometric, etc.), apparatus for microwave measurements.

It will be appreciated that various other configurations of the liquid permeable and the gas permeable portions of the PMPM device may be envisioned without departing from the present technology.

In some embodiments, the PMPM devices of the present technology may comprise a pressure sensor. In some instances, the pressure sensor is in operative contact with the polymer swellable solution so as to measure pressure in the polymer swellable solution. For example, as shown in FIG. 2, pressure sensor 100 may be in contact with the polymer swellable solution 70 so as to monitor pressure in the inner chamber 64. In some instances, the pressure sensor may be a digital sensor with compensation for temperature or without compensation for temperature. In some other instances, the pressure sensor may be a differential pressure sensor or may be an absolute pressure sensor or a strain sensor. In some instances, the pressure sensor is placed on the porous medium parameter measurement device so as to be completely buried in the porous medium in use, whereas in some other instances, the pressure sensor may be partially out of porous medium in use.

In some embodiments, the PMPM devices of the present technology comprise a controller. The controller may in the form of a printed circuit board (PCB). The controller may perform various activities such as acquiring, storing, processing, transmitting and/or communicating different soil parameters obtained from sensors of the porous medium measurement device. Examples of different soil parameters that may be processed by the controller include, but are not limited to, the voltage from pressure, temperature, conductance, conductivity, atmospheric pressure, and any other variables. In some instances, the controller may communicate through wiring means (e.g., cable) or wirelessly to a computer at a remote location. In some instances data obtained by the controller may be transmitted to the computer at fixed interval or only when a variation (e.g., in percentage, or in kPa) occurs. The controller may be powered by a rechargeable energy source placed into the controller or remotely from the controller (e.g., in other parts of the PMPM device). The controller may be equipped with a temperature sensor for measuring temperature of the porous medium.

Although the PMPM devices of the present technology have been described primarily for measurement of parameters of culture media, and in particular in relation to measurement of water tension in soil, it is to be appreciated that the PMPM devices of the present technology could be applied to measure similar parameters in a reservoir, retention basin, indoor culture, lake, or the like.

In some embodiments, the PMPM devices of the present technology may comprise more than one inner chamber comprising a polymer swellable solution having different polymer concentrations.

INCORPORATION BY REFERENCE

All references cited in this specification, and their references, are incorporated by reference herein in their entirety where appropriate for teachings of additional or alternative details, features, and/or technical background.

EQUIVALENTS

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following embodiments.

The invention claimed is:

1. A porous medium parameter measurement device comprising:
   i) a liquid permeable portion comprising a liquid permeable component and a polymer swellable solution;
   ii) a gas permeable portion comprising a gas permeable component;
   wherein the liquid permeable portion is in operative communication with the gas permeable portion through the gas permeable component; and
   wherein the gas permeable component acts to purge gases from the liquid permeable component and the polymer swellable solution.

2. A porous medium parameter measurement device as defined in claim 1, wherein the gas permeable component is in operative communication with the porous medium.

3. A porous medium parameter measurement device as defined in claim 1, wherein the gas permeable component is in gas communication with the porous medium.

4. A porous medium parameter measurement device as defined in claim 1, wherein the gas permeable component acts to purge gases trapped in: i) the liquid permeable component, ii) the polymer swellable solution, or iii) both i) and ii).

5. A porous medium parameter measurement device as defined in claim 1, wherein the porous medium is soil.

6. A porous medium parameter measurement device as defined in claim 1, wherein the porous medium parameter is water tension in the porous medium.

7. A porous medium parameter measurement device as defined in claim 1, wherein the porous medium parameter is ionic concentration.

8. A porous medium parameter measurement device as defined in claim 1, wherein the liquid permeable portion is impermeable to gases.

9. A porous medium parameter measurement device as defined in claim 1, wherein the liquid permeable portion is impermeable to air.

10. A porous medium parameter measurement device as defined in claim 1, wherein the gas permeable portion is permeable to gas and impermeable to liquids.

11. A porous medium parameter measurement device as defined in claim 1, wherein the gas permeable portion is permeable to air and impermeable to liquids.

12. A porous medium parameter measurement device as defined in claim 1, wherein the gas permeable component is in contact with the liquid permeable component.

13. A porous medium parameter measurement device as defined in claim 1, wherein the gas permeable component is in contact with the polymer swellable solution.

14. A porous medium parameter measurement device as defined in claim 1, wherein the gas permeable component is in contact with the liquid permeable component and the polymer swellable solution.

15. A porous medium parameter measurement device as defined in claim 1, wherein the gas permeable component is in operative communication with the liquid permeable component.

16. A porous medium parameter measurement device as defined in claim 1, wherein the gas permeable component is in operative communication with the polymer swellable solution.

17. A porous medium parameter measurement device as defined in claim 1, wherein the gas permeable component is in operative communication with the liquid permeable component and the polymer swellable solution.

18. A porous medium parameter measurement device as defined in claim 1, wherein the gas permeable portion is hydrophobic.

19. A porous medium parameter measurement device as defined in claim 1, wherein the gas permeable component is a hydrophobic membrane.

20. A method for measuring a porous medium parameter, the method comprising:
  a) inserting the porous medium parameter measurement device as defined in claim 1 into a porous medium comprising a porous medium solution;
  b) allowing the porous medium solution to diffuse through the porous medium parameter measurement device; and
  c) measuring a porous medium parameter from the porous medium solution comprised in the porous medium parameter measurement device.

\* \* \* \* \*